US 6,623,040 B1

(12) United States Patent
Foley et al.

(10) Patent No.: US 6,623,040 B1
(45) Date of Patent: *Sep. 23, 2003

(54) METHOD FOR DETERMINING FORCED CHOICE CONSUMER PREFERENCES BY HEDONIC TESTING

(75) Inventors: Mary M. Foley, The Colony, TX (US); Beaufort M. Lancaster, Lewisville, TX (US)

(73) Assignee: Recot, Inc., Pleasanton, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/922,599

(22) Filed: Sep. 3, 1997

(51) Int. Cl.[7] ............................................. G09B 29/00
(52) U.S. Cl. .......................... 283/67; 283/56; 283/70; 434/365
(58) Field of Search ................. 283/56, 67, 70; 434/365

(56) References Cited

U.S. PATENT DOCUMENTS

| | | | |
|---|---|---|---|
| 4,908,758 A | 3/1990 | Sanders | 364/300 |
| 5,090,734 A | 2/1992 | Dyer et al. | 283/67 |
| 5,191,896 A | 3/1993 | Gafni et al. | 128/742 |

OTHER PUBLICATIONS

Cardello and Maller, *Relationships Between Food Preferences and Food Acceptance Ratings*, Journal of Food Science, vol. 47, pps. 1553–1557, 1561 (1982).
Peryam and Girardot, *QM Pins Food "Likes" and "Dislikes" With Advanced Taste–Test Method*, Food Engineering, pps. 56–61, (1952).
Peryam and Pilgrim, *Hedonic Scale Method of Measuring Food Preferences*, Food Engineering, vol. XI, No.9, pp. 1–6, (1957).
Civille et al., *Sensory Evaluation Guide for Testing Food and Beverage Products*, Food Technology, pp. 50–59 (Nov. 1981).
Agresti, A., "Models For Binary Response Variables" in *Catagorical Data Analysis*, John Wiley & Sons, Inc. (A Wiley–Interscience Publication), University of Florida, Gainesville, Florida, 1990, pp. 79–88.
SAS Institute Inc., *SAS/STAT® User's Guide, Version 6, Fourth Edition*, vol. 2, Cary, NC: SAS Institute Inc., Chapter 27 "The Logistic Procedure", 1071–1108 (1990).
Stone, PhD., H., "The Paired Preference Method: What You See Is Not Always What You Get", *Sensory forum*, The Society of Food Science and Technology, No. 70, (May 1996).
XP–002089508 *Sweetening of Soft Drinks with Mixtures of Sugars and Saccharin*, Hyvönen, et al., Institute of Food Technologists, 1989.
XP–002089509 *Alternative Hedonic Measures*, Vie et al., Journal of Food Science, vol. 56, No. 1, pp. 1–5, 1991.

*Primary Examiner*—A. L. Wellington
*Assistant Examiner*—Mark T. Henderson
(74) *Attorney, Agent, or Firm*—Rothwell, Figg, Ernst & Manbeck

(57) ABSTRACT

The present invention recognizes and takes advantage of the fact that there is a correlation between a consumer's overall like or dislike of two particular products (hedonic test results), each evaluated individually, and the likelihood that the consumer will choose one product over the other (forced choice test results) in a forced choice comparison. Taking advantage of this correlation, it is possible to determine the likelihood that a consumer will choose one product over another product of the same type simply by conducting hedonic testing and without specifically conducting forced choice testing.

5 Claims, 3 Drawing Sheets

METHOD FOR DETERMINING FORCED CHOICE CONSUMER PREFERENCES BY HEDONIC TESTING

FIELD OF THE INVENTION

The invention relates to consumer testing in general and, more particularly, to consumer preference testing.

BACKGROUND OF THE INVENTION

In consumer testing, e.g., testing that a company conducts to determine how well its product will be received by the intended consumer group, there are a number of different testing protocols that are followed. In hedonic testing, a consumer is presented with product samples, e.g., salty snacks such as pretzels or potato chips; cookies; toilet paper; etc., and is asked to evaluate each of several different products of a given type on a number of different qualities or product characteristics. For example, the test subject may be asked to evaluate potato chips for saltiness, flavor, appearance, texture, "mouth feel," etc.

When conducting hedonic testing, it is customary to have the test subject rate each parameter on a Likert scale, i.e., a scale having discrete integer values ranging from a low value (e.g., disliked extremely) to a high value (e.g., liked extremely). Likert scales for hedonic testing typically require a response from 1 to 5, 1 to 7, or 1 to 9. For consumer testing of food products, a nine-point Likert scale customarily is used, with a response of 9 indicating that the consumer liked the particular quality being evaluated extremely; a response of 8 indicating that the consumer liked the quality being evaluated very much; 7 indicating that the consumer liked it moderately; 6 indicating that the consumer liked the quality slightly; 5 indicating that the consumer neither liked nor disliked the quality; 4 indicating that the consumer disliked the quality slightly; 3 indicating that the consumer disliked it moderately; 2 indicating that the consumer disliked it very much; and 1 indicating that the consumer disliked the quality being evaluated extremely. In addition to evaluating the individual qualities, the test subject typically is asked to provide a Likert scale rating indicating how well he or she liked the product overall, i.e., taking into account all factors or qualities which he or she has been or will be asked to evaluate.

Usually, the test subject is asked to indicate his or her liking or evaluation of the same characteristics or qualities of several products of the same type, e.g., several brands of pretzels or cookies. In sequential monadic testing, the consumer provides a complete evaluation for a given product before providing a complete evaluation for another product. In other words, a consumer testing potato chips, for example, indicates his or her liking of the taste, crunch, saltiness, aroma, and overall liking of brand X potato chips, then indicates his or her liking of the taste, crunch, saltiness, aroma, and overall liking of brand Y potato chips. (This is in contrast to having a consumer provide a response for, e.g., the taste of brand X, then the taste of brand Y, then the crunch of brand X, then the crunch of brand Y, then the saltiness of brand X, then the saltiness of brand Y, etc.)

Finally, when the consumer has completed his sequential monadic evaluation of all the products being tested—typically no more than three or four different products are tested in a given test setting—the consumer is asked to indicate which of two given products he or she likes better, e.g., whether he likes W or X better; whether he likes W or Y better; whether likes W or Z better; whether he likes X or Y better; whether he likes X or Z better; and whether he likes Y or Z better. This latter testing is referred to as forced choice testing, i.e., the consumer is forced to choose which product he or she prefers from among a forced selection of two possible products.

In certain situations, it is not possible or feasible to conduct forced choice testing, e.g., when the product flavors are so strong that tasting more than two products, or tasting the products a second time to select a preference, is precluded. Alternatively, time limitations may be such that adding the task of additional forced-choice comparisons among all combinations of products is unreasonable and/or excessive. Thus, in such situations, it may be difficult to obtain meaningful forced choice data. For example, as the number of products being evaluated increases, so too does the number of possible forced choice pairings, but at a faster rate than the number of products increases. Other difficulties or problems with forced choice testing include the following: 1) the most accurate and reliable product assessment generally is considered to be the initial reaction to the product, not a response that comes after answering questions about individual taste, appearance, and texture details, etc.; 2) the respondents' decreasing memory of the samples becomes problematic if the samples are not available for re-sampling, but sensory fatigue (overload of the taste senses) becomes an issue if they are; and 3) the last product seen and sampled and the last question asked may influence the preference unevenly.

SUMMARY OF THE INVENTION

In the present invention, we have recognized and taken advantage of the fact that there is a correlation between a consumer's overall like or dislike of two particular products (hedonic test results), each evaluated individually, and the likelihood that the consumer will choose one product over the other (forced choice test results) in a forced choice comparison. Thus, it is possible to determine the likelihood that a consumer will choose one product (product A) over another product (product B) of the same type simply by conducting hedonic testing and without specifically conducting forced choice testing.

Thus, according to a first aspect of the invention, a method is provided for determining forced-choice preference information from hedonic test data. The method entails obtaining a test group of human test subjects and providing each of the test subjects in the group with two or more test samples. The test subjects are asked to sample each of the two or more test samples and provide hedonic test data indicative of how well they liked each of the test samples. The hedonic test data is then processed from all of the test subjects to determine at least one predicted forced choice preference result, the predicted forced choice preference result being indicative of the likelihood that a test subject would select one of the test samples over another one of the test samples in a forced choice comparison between a selected pair of test samples.

In a preferred embodiment of the method of the invention, of a pair of test samples being compared, a stronger test sample and a weaker test sample are determined. For each test subject, an overall-liking difference value is determined, the overall-liking difference value being based on the overall-liking value the given test subject assigned to the stronger test sample minus the overall-liking value the given test subject assigned to the weaker test sample. Then, for each possible overall-liking difference value, the number of occurrences of that possible value is determined. For each possible overall-liking difference value, the number of occurrences of that value is multiplied by a probability coefficient to determine a corresponding subset number which represents the number of test subjects in a correlative, proportionate subset of the test subjects yielding that particular possible overall-liking difference value that would choose the stronger test sample over the weaker test sample in a forced choice comparison between the two. The subset numbers corresponding to each of the possible overall-liking difference values are then totaled to determine the total number of test subjects who would choose the stronger test sample over the weaker test sample in a forced choice comparison between the two. The preference for the stronger test sample may then be expressed by dividing the total number of subjects who would choose the stronger test sample over the weaker test sample in a forced choice comparison by the number of test subjects in the whole test group.

Preferably, the stronger test sample is the one of the two samples being compared with the larger average or mean overall-liking value. Furthermore, it is preferable for the hedonic test data to be obtained in integral, Likert scale format such that the overall-liking difference value, which equals the overall-liking value for the stronger test sample minus the overall-liking value for the weaker test sample, falls within a range of discrete integer values.

Thus, by utilizing the method according to the invention, the drawbacks to forced choice comparison testing noted above are substantially avoided.

DETAILED DESCRIPTION OF THE INVENTION

Figure 1:
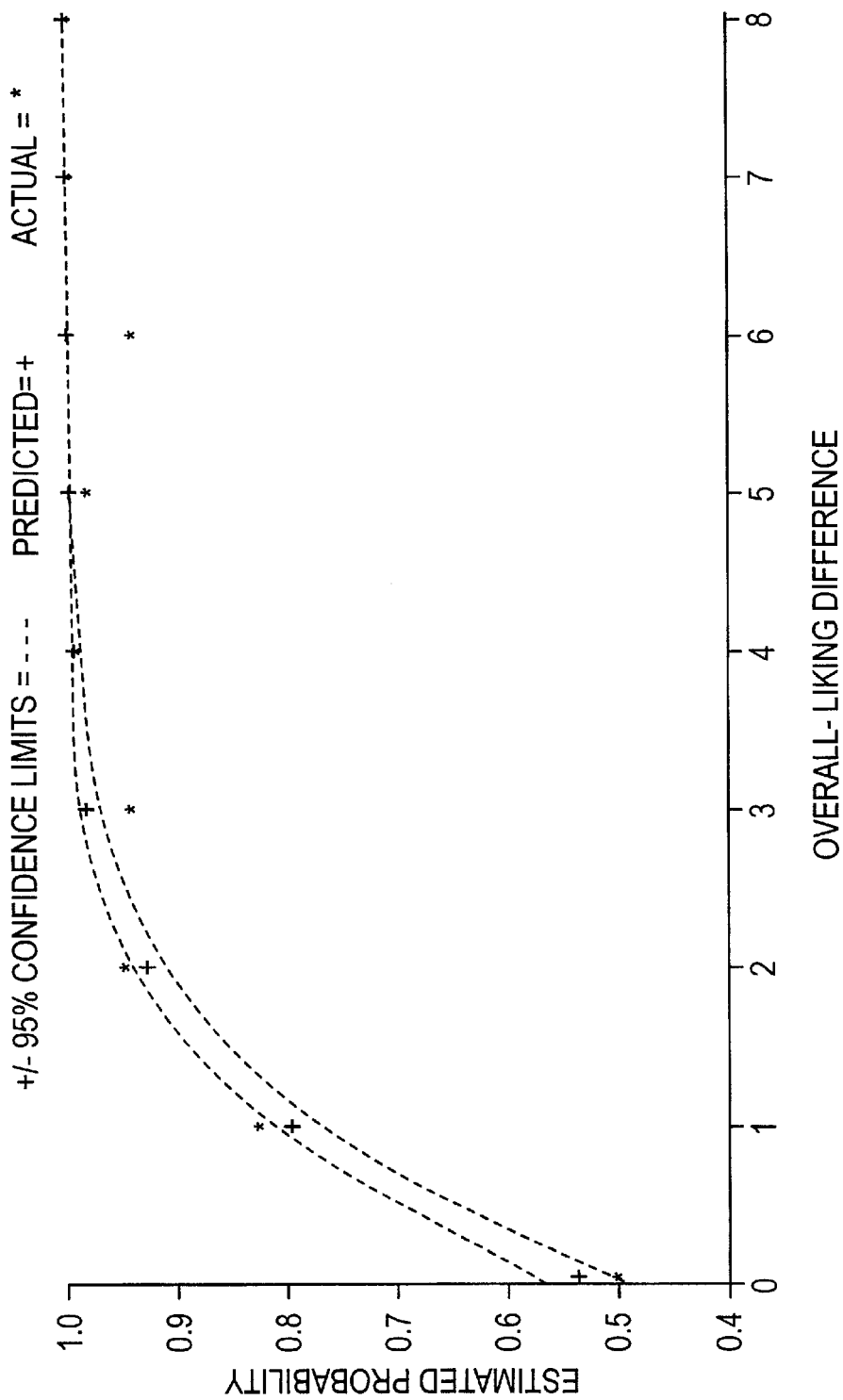
FIG. 1 is a graph showing the correspondence between actual measured preference proportion values and preference proportion values determined by logistic regression analysis thereof.

As noted above, the invention recognizes and takes advantage of the fact that there is a correlation between the hedonic test score a test subject gives for the overall likability of each of two different products and the likelihood that the test subject will choose one product over the other. Specifically, we have discovered that the greater the difference in overall liking of two different products (as measured on a hedonic scale), the greater the probability that a test subject (i.e., a consumer) will choose, in a forced choice preference situation, the product to which he or she assigned the greater overall liking score.

For purposes of understanding our invention, we believe it is preferable to explain or demonstrate how our approach is used in practice, and then to explain how the model we use in our method was developed.

Conducting the Testing

First, a number of respondents or test subjects that is large enough to obtain accurate product evaluation scores, i.e., on the order of sixty to one hundred twenty, is determined according to standard statistical analysis and consumer testing protocols and obtained. When conducting the tests, each respondent is asked to evaluate two or more samples of the same type of product, e.g., two or more different brands of potato chips, cookies, bagels, etc. To ensure meaningfulness of the test results, it is generally necessary that the respondents be users of the specific products or product category being tested. The respondents evaluate one sample at a time, completing a questionnaire for each sample before evaluating the next product. In other words, the testing is conducted in sequential monadic fashion. The products should not be labeled or branded, i.e., there should be "blind" presentation of the samples. The serving order should be balanced, i.e., each possible serving order should be used equally. If this is not possible, each sample product should be presented as the first sample an equal number of times.

The first survey question should ask about the respondent's overall liking of the product and, for food products, for example, may be worded along the lines of "Considering everything about this sample—appearance, flavor, and texture—how well do you like it overall?" The respondent provides his or her response, preferably on a nine point Likert scale as described above. The respondent may then be asked a number of other questions pertaining to specific attributes of the product. No forced choice preference question is asked.

Once all respondents have been tested, forced choice preferences are determined as follows. First, the average overall-liking score for each product (the sum of all respondents' overall-liking scores for a given product divided by the total number of respondents) is calculated. Two different products for which it is desired to calculate the forced choice preference are then selected. Of these two products, the one having the larger average overall-liking score is designated the "stronger product" (or "product A"), and the other is designated the "weaker product" (or "product B").

The overall-liking difference between product A and product B is then determined for each respondent by subtracting each respondent's product B overall-liking score from his or her product A overall-liking score. Because the preferred scale is a 1–9 Likert scale on which only integer responses are possible, the overall-liking difference for each respondent will range from a highest possible value of 8 (indicating that the particular respondent liked product A extremely and assigned it an overall-liking value of 9 and disliked product B extremely and assigned it an overall-liking value of 1) to a lowest possible value of –8 (indicating that the particular respondent liked product B extremely and disliked product A extremely).

Once all respondents' overall-liking difference values have been determined for each of the two products being compared, a "frequency table" is developed, i.e., the number of respondents demonstrating each of the possible overall-liking difference values (product A overall-liking value minus product B overall-liking value) is determined. This is shown by the information in column 1 (overall-liking difference, product A over product B) and column 2 (number of respondents yielding a particular overall-liking difference value) in Table I below, which presents an exemplary set of data. The respondents' specific overall-liking scores are not important—just the difference between them. Thus, a respondent who gives product A an 8 and product B a 6 is counted in the "2 bucket" of the "frequency table" to the same extent a respondent who gives product A a 5 and product B a 3 is.

TABLE I

| (1)<br>Overall-Liking<br>Difference | (2)<br>Number of<br>Respondents | (3)<br>Probability<br>Coefficient | (4)<br>Portion<br>Preferring A |
|---|---|---|---|
| −8 | 1 | 0.00004 | 0.00004 |
| −7 | 0 | 0.00015 | 0.00000 |
| −6 | 4 | 0.00051 | 0.00204 |
| −5 | 5 | 0.00176 | 0.00880 |
| −4 | 3 | 0.00608 | 0.01824 |
| −3 | 10 | 0.02076 | 0.20760 |
| −2 | 12 | 0.06849 | 0.82188 |
| −1 | 15 | 0.20316 | 3.04740 |
| 0 | 20 | 0.53073 | 10.61460 |
| 1 | 10 | 0.79684 | 7.96840 |
| 2 | 12 | 0.93151 | 11.17812 |
| 3 | 9 | 0.97924 | 8.81316 |
| 4 | 9 | 0.99392 | 8.94528 |
| 5 | 8 | 0.99824 | 7.98592 |
| 6 | 0 | 0.99949 | 0.00000 |
| 7 | 1 | 0.99985 | 0.99985 |
| 8 | 0 | 0.99996 | 0.00000 |
| | total<br>respondents:<br>119 | | Total<br>preferring<br>product A:<br>60.61;<br>Preference<br>for product<br>A: 50.93% |

After determining the number of respondents (Col. 2) yielding each possible overall-liking difference value (Col. 1), the number of respondents for each overall-liking difference value is multiplied by an empirically derived probability coefficient (Col. 3) to obtain, for each overall-liking difference value, the portion or subset of respondents who would prefer the stronger product, i.e., product A. (The manner in which the probability coefficients are determined is described below.) Thus, each probability coefficient represents the likelihood that a given respondent, for whom the difference between his or her overall-liking of product A and product B is a particular value, would prefer product A to product B if forced to choose between the two.

In other words, referring to exemplary Table I, out of 100,000 people each yielding an overall-liking difference of, for example, −8 (i.e., they disliked product A extremely and assigned it an overall-liking value of 1, but liked product B extremely and assigned it an overall-liking value of 9), only four seemingly would contradict their respective ratings and choose product A over product B when forced to chose between the two. On the other hand, out of 100,000 respondents for each of whom the overall-liking difference value is 8 (i.e., they liked product A extremely and gave it an overall-liking value of 9, but disliked product B extremely and gave it an overall-liking value of 1), 99,996 actually would choose product A over product B when forced to choose between the two. Hence, the number of respondents yielding a given overall-liking difference value multiplied by the probability coefficient for that overall-liking difference value yields the portion or subset of that group of respondents that would choose product A over product B in a forced choice comparison between the two (mindful of the fact that fractional numbers of people cannot exist, but realizing that, for much larger test populations than the 119 respondents whose test results are reflected in Table I, "fractional people" become negligible).

(With respect to the probability coefficient corresponding to an overall-liking difference of zero, one might expect the probability coefficient to be 0.5000, indicating that half the population would select product A in a forced choice scenario and half the population would select product B in a forced choice scenario. The fact that this is not the case is believed to result from the fact that the probability coefficients are determined by curve-fitting empirical data, as explained below. It is also believed to reflect the fact that the Likert scale is discrete, i.e., it permits only integer values to represent the respondents' like or dislike of a given product, whereas a continuous scale would have allowed the respondents to show slightly greater or slightly less like of one product, which would be consistent with the slightly greater preference for product A represented by the probability coefficient being slightly greater than 0.5000.)

After the portion or subset of respondents that would select product A over product B is determined for each overall-liking difference value (Col. 4), the portion values are totaled to obtain the total number of respondents that would select product A over product B in a forced choice comparison. With respect to Table I, it is predicted that 60.61 respondents out of the 119 whose sample test data are reflected in Table I would have chosen product A over product B in a forced choice comparison. This represents a 50.93% preference for product A (60.61÷119) or, in other words, 5,093 respondents out of 10,000 would select product A over product B in a forced choice comparison.

It should be appreciated that this methodology can be used to predict the likelihood that any one product selected from a group of several sample products will be selected over any other product selected from the same group of sample products without actually having to conduct the various permutations of forced choice comparisons. The limit, if any, of the number of sample articles for which such forced choice comparison data can be calculated meaningfully from the Likert scale test data is not presently known.

Determination of Probability Coefficients

As noted above, the probability coefficients used in the method are empirically derived. To develop the set of probability coefficients (Column 3 of Table I above) and to verify the accuracy of this novel approach to determining forced choice preferences, fifty-six central location tests were conducted covering a wide range of snack food-type products, namely, potato chips, novelty puffs, tortilla chips, dip/salsa, seasoned tortilla chips, tortillas, and multi-grain chips. The number of tests and the number of test subjects (respondents) for each type of product tested for purposes of developing the probability coefficients is indicated in Table II below.

TABLE II

| Product Type | Number of Tests | Number of Subjects |
|---|---|---|
| potato chips | 6 | 702 |
| novelty puffs | 1 | 119 |
| tortilla chips | 2 | 233 |
| dip/salsa | 5 | 559 |
| seasoned tortilla chips | 1 | 118 |
| tortillas | 3 | 313 |
| multi-grain chip | 2 | 236 |

In each test, between sixty and one hundred twenty-one respondents evaluated two different product samples. Samples were served in plain white soufflé cups coded with the same three-digit number for both the hedonic scale and the preference questions. The test subjects answered the hedonic scale questions with the samples presented in sequential monadic fashion, balanced for presentation order.

When being asked the forced choice preference question, respondents were presented with the same two sample products simultaneously, with an opportunity for re-tasting if desired.

Variables that differed between samples being compared included product brand, line quality product versus gold standard product, different oils and/or seasonings, and even a new fryer configuration versus an older fryer configuration. The large variety of products and test conditions (test parameters) was used so that the conclusions from the modeling, i.e., the probability coefficients, would be more broadly applicable. In other words, the probability coefficients developed by the testing discussed herein probably could be used for all different types of snack food products, if not for all different types of food products in general. (We do not know, however, whether the probability coefficients disclosed herein could be used to obtain forced choice preference data for products that are quite different from snack food products, e.g., cars or televisions.) If the number of different products included in developing the probability coefficients was statistically small, the validity of our conclusions would be much more restricted.

The composite forced choice preference test results from the twenty different tests summarized in Table II then were processed to determine, for each possible overall-liking difference value, the number of test subjects who yielded that overall-liking difference value, as shown in Columns 1 and 2 of Table III below.

TABLE III

| Overall-Liking Difference Value | Number of Subjects | Subjects Choosing Product with Higher Overall-Liking Value | Proportion |
|---|---|---|---|
| 0 | 591 | 291* | 0.492 |
| 1 | 809 | 671 | 0.829 |
| 2 | 442 | 419 | 0.948 |
| 3 | 202 | 190 | 0.941 |
| 4 | 115 | 114 | 0.991 |
| 5 | 68 | 67 | 0.985 |
| 6 | 35 | 33 | 0.943 |
| 7 | 15 | 15 | 1 |
| 8 | 3 | 3 | 1 |

*This is the number that chose the sample with the higher mean acceptability, i.e., the stronger product of the two being compared in any given forced choice comparison.

(The "Number of Subjects" might actually more properly be designated "Number of Occurrences" since it is the actual number of times a given overall-liking difference value occurred, and that particular value could have been demonstrated more than once by a given test subject or respondent if that test subject or respondent participated in more than one test, e.g., by testing more than one product type.)

The proportion of respondents (Column 4 of Table III) who, in the forced choice comparisons, chose the product to which he or she had assigned the higher overall-liking value was then determined by dividing the number of subjects who, in the forced choice comparison, picked the product to which he or she had assigned the higher overall-liking value (Column 3 of Table III) by the number of subjects exhibiting the given overall-liking difference value (or the number of occurrences of that value), i.e., Column 2 of Table III. (Like the "Number of Subjects" demonstrating a particular overall-liking difference value (Column 2 of Table III), the "Number of Subjects Choosing the Product With the Higher Overall-Liking Value" (Column 3 of Table III) might also more properly be termed the number of occurrences of a test subject choosing the more well-liked product for the same reason explained above.)

Once the proportion (Column 4 of Table III) of subjects choosing, in a forced choice comparison, the product to which he or she assigned the higher overall-liking value was determined for each possible overall-liking difference value, a dose-response curve was determined using logistic regression analysis, with each overall-liking difference value constituting an abscissa or x-axis value and the corresponding proportion constituting the ordinate or y-axis value. (It should be noted that no negative overall-liking difference values were considered in this step of the analysis since the focus of the analysis at this point was on respondents who, in the forced choice comparison, chose the product to which they had assigned the greater overall-liking value, not the respondents who seemingly contradicted themselves and chose the product to which they had assigned the lower overall-liking value.) The linear logit regression model (Agresti, 1990) was chosen to model or curve-fit this system because it is appropriate for logistic regression analysis when the response variable (the proportion who, in the forced choice comparison, chose the product to which they had assigned the higher overall-liking value) is binomial. (The response variable here was binomial in the sense that the subjects did or did not choose the sample to which they had assigned the higher overall-liking value.)

The linear logit model can be written in general as:

$$\ln[p/(1-p)] = \alpha + \beta x, \qquad (1)$$

where p is the proportion choosing the higher overall-liking value product in the forced choice comparison (Column 4 of Table III), i.e., the response or y-axis value;

α is a constant;

x is the dose or abscissa value, i.e., the overall-liking difference value (Column 1 of Table III); and β is a coefficient of the x-axis variable.

The logistic regression procedure PROC LOGISTIC from the SAS statistical software package (SAS Institute, 1990) was then used to estimate the constant α and the coefficient β in the equation above as α=0.1231 and β=1.2435. The model equation then becomes $$\ln[p/(1-p)] = 0.1231 + 1.2435x \text{ or,} \qquad (2)$$

$$p = \frac{e^{(0.1231+1.2435x)}}{e^{(0.1231+1.2435x)} + 1} \qquad (3)$$

Equation (3), which was derived by curve-fitting empirically determined data, was then used to calculate the predicted proportion value for each of the non-negative overall-liking difference values, as shown in Column 3 of Table IV below. THESE ARE THE PROBABILITY COEFFICIENTS SHOWN IN COLUMN 3 OF TABLE I FOR THE NON-NEGATIVE OVERALL-LIKING DIFFERENCE VALUES (shown to three decimal places) AND USED IN ACTUALLY CONDUCTING A "LIVE" TEST AS DESCRIBED ABOVE.

TABLE IV

| Overall-Liking Difference Value | Measured Proportion (From Table III) | Predicted Proportion | 95% Confidence Limits |
|---|---|---|---|
| 0 | 0.492 | 0.531 | 0.493–0.568 |
| 1 | 0.829 | 0.797 | 0.776–0.816 |
| 2 | 0.948 | 0.932 | 0.915–0.945 |

TABLE IV-continued

| Overall-Liking Difference Value | Measured Proportion (From Table III) | Predicted Proportion | 95% Confidence Limits |
|---|---|---|---|
| 3 | 0.941 | 0.979 | 0.970–0.986 |
| 4 | 0.991 | 0.994 | 0.990–0.996 |
| 5 | 0.985 | 0.998 | 0.997–0.999 |
| 6 | 0.943 | 0.999 | 0.999–1.000 |
| 7 | 1 | 1 | 0.9996–1.000 |
| 8 | 1 | 1 | 0.9999–1.000 |

Column 4 of Table IV shows the 95% confidence limits for the predicted proportions in column 3 of Table IV. In other words, if this analysis were conducted one hundred times using one hundred independent sets of data, ninety-five of the calculated predicted proportions (column 3 of Table IV) would be between 0.493 and 0.560 for an overall liking difference value of 0, for example. The same applies for each row of the table as well. Graphically, FIG. 1 shows how close the predicted proportion values (calculated from Equation (3)) are to the actual proportion values as measured by the test data.

The predicted proportion values (Column 3 of Table IV) are then "extended" to cover negative overall-liking difference values by assuming "symmetry." In other words, because a negative overall-liking difference value indicates that a particular respondent assigned a higher overall-liking value to the weaker product or product B than to the stronger product or product A (recalling that the designation of one product as the stronger product (product A) and the other as the weaker product (product B) is based on the two products' relative average overall-liking values), the probability that a respondent for whom the overall-liking difference value is negative would choose product A in a forced choice comparison is assumed to be one minus the probability that a respondent for whom the overall-liking difference value is positive and of the same absolute value would choose product A in a forced choice comparison. To demonstrate this symmetry by way of an example, the predicted proportion corresponding to an overall-liking difference value of 2 is 0.932 (Column 3 of Table IV); the predicted proportion corresponding to an overall-liking difference value of −2 is 1−0.932, or 0.068 as expressed to three decimal places.

Thus, the complete set of probability coefficients (representing the probability that product A would be chosen over product B in a forced choice comparison) is shown in Table V to three decimal places, and these probability coefficients are the same probability coefficients shown in Table I, above, to five decimal places.

TABLE V

| Overall-Liking Difference Value (Product A-Product B) | Probability of Product A Being Chosen | Overall-Liking Difference Value (Product A-Product B) | Probability of Product A Being Chosen |
|---|---|---|---|
| −8 | 0 | 1 | 0.797 |
| −7 | 0 | 2 | 0.932 |
| −6 | 0.001 | 3 | 0.979 |
| −5 | 0.002 | 4 | 0.994 |
| −4 | 0.006 | 5 | 0.998 |
| −3 | 0.021 | 6 | 0.999 |
| −2 | 0.068 | 7 | 1 |
| −1 | 0.202 | 8 | 1 |
| 0 | 0.531 | | |

Figure 2:
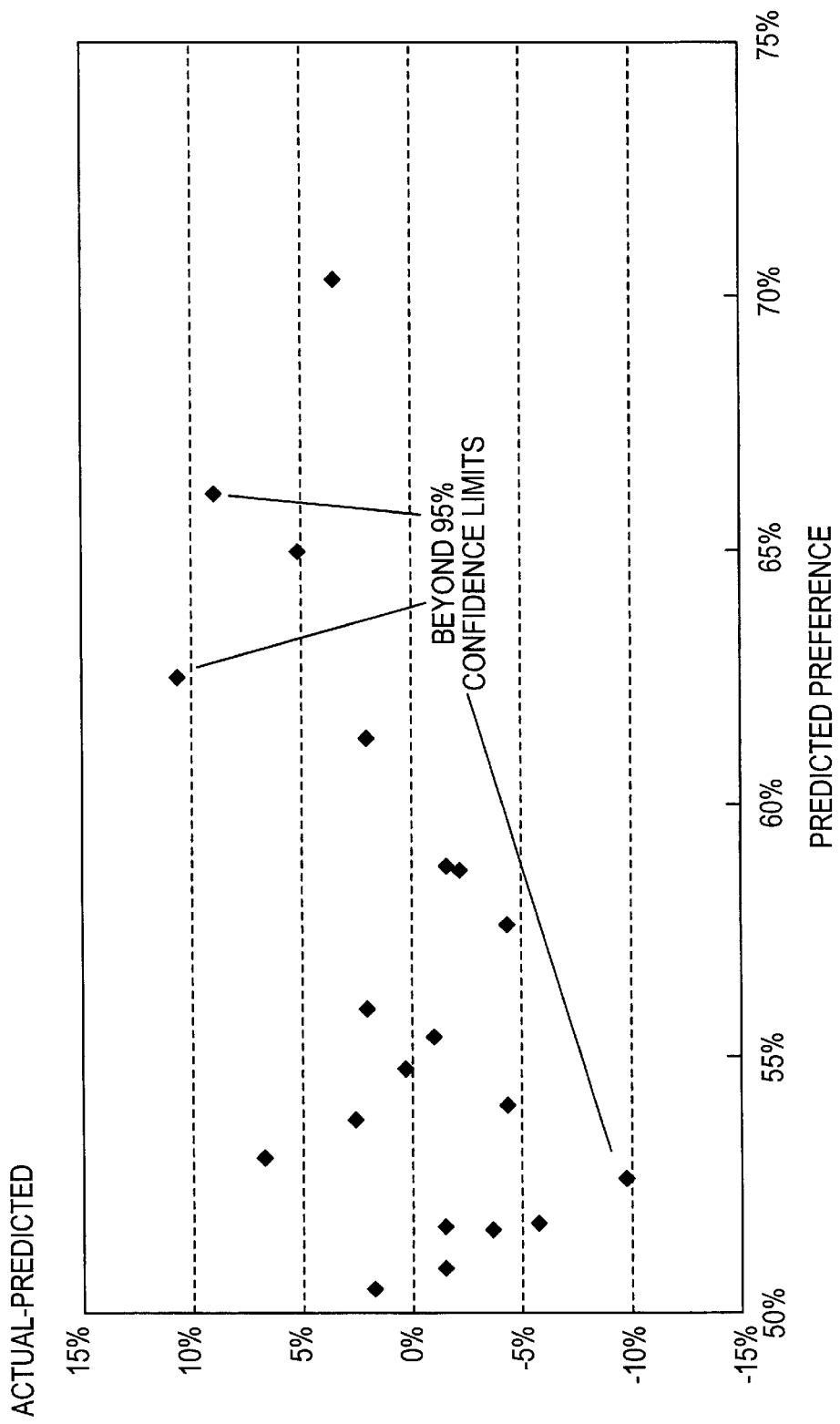
FIGS. 2 and 3 are scatterplots showing the error between predicted preference values and actual preference values for consumer tests used to develop the model of the invention and to test the model, respectively.
Figure 3:
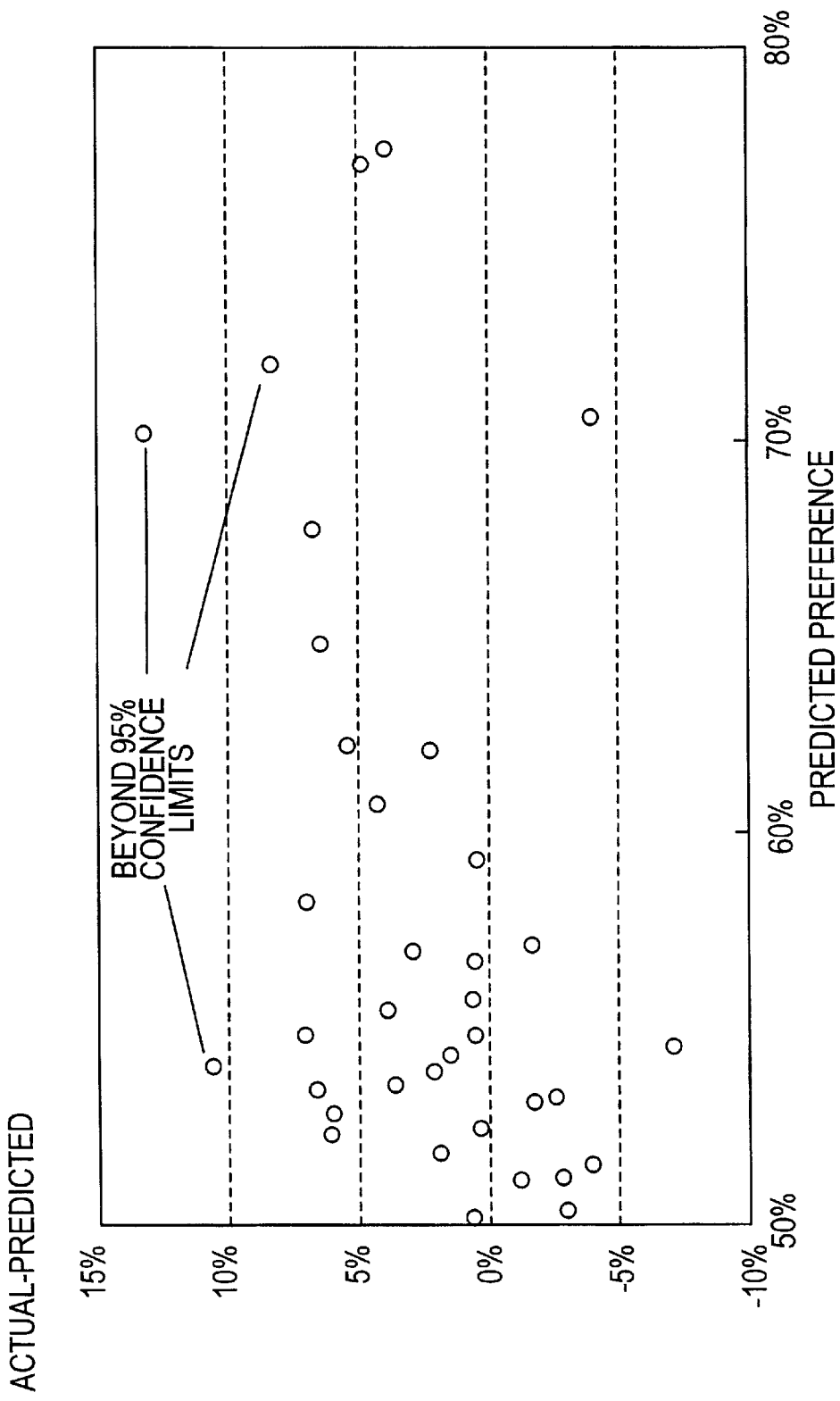

Finally, the accuracy of our novel approach to deriving forced choice comparison information from hedonic testing data is illustrated in FIGS. 2 and 3. FIG. 2 is a scatterplot showing the difference between the actual (i.e., measured) forced choice comparison result and the predicted (i.e., calculated by our method) forced choice comparison result for each of the twenty tests summarized in Table II above and used to estimate α and β in equation (1) above. In each case, the predicted value was for the sample having the higher average overall-liking value, i.e., the stronger product or product A. Seventeen of the twenty actual forced choice preference values have 95% confidence intervals that extend so as to include the forced choice comparison results predicted by our model.

Moreover, because one reasonably would expect to see such close correlation when making the comparison using the tests on which the model coefficients were based, we also used our model to calculate forced choice comparison results for thirty-six additional central location tests, the results of which were not used in deriving the probability coefficients. Those thirty-six tests are summarized in Table VI below.

TABLE VI

| Product Type | Number of Tests | Number of Subjects |
|---|---|---|
| potato chips | 7 | 813 |
| cookies | 6 | 639 |
| tortilla chips | 7 | 795 |
| dip/salsa/picante | 6 | 673 |
| Mexican foods | 3 | 268 |
| tortillas | 2 | 230 |
| multi-grain chips | 1 | 120 |
| pretzels | 4 | 427 |

FIG. 3 is a scatter plot, similar to FIG. 2, showing for each of the thirty-six tests summarized in Table VI the difference between the actual forced choice comparison result and the result predicted by our model. Thirty-three of the 95% confidence intervals for these thirty-six actual preference percentages extend so as to include the preference percentage predicted by our model. Thus, out of fifty-six total tests (20 used to generate the model and thirty-six used to "test" it), only six yielded predicted preference percentage values not within the 95% confidence interval of the actual test result value. These discrepancies are almost completely accounted for by large deviations from a 50/50 split among subjects showing no difference in overall-liking values.

It will be appreciated by those having skill in the art that the concepts and methodologies disclosed herein can be extended in numerous ways, and such extensions of our approach are deemed to be within the scope of the following claims.

What is claimed is:

1. A method for determining forced-choice preference information, said method comprising:

obtaining a test group, said test group comprising a plurality of human test subjects;

providing each of said test subjects with two or more test samples;

causing each of said test subjects to sample each of said two or more test samples;

obtaining from each of said test subjects hedonic test data indicative of how well each of said test subjects liked each of said test samples, wherein said hedonic test data comprises overall-liking values assigned by each of said test subjects to each of said test samples; and processing the hedonic test data from all of said test subjects to determine at least one predicted forced choice preference result, said at least one predicted forced choice preference result being indicative of the likelihood that a test subject would select one of said test samples over another of said test samples in a forced choice comparison of a pair of said test samples, wherein said processing comprises:

of said pair of test samples, determining a stronger test sample and a weaker test sample;

for each of said test subjects, determining an overall-liking difference value, the overall-liking difference value for a given test subject being determined based on the overall-liking value said given test subject assigned to the stronger test sample minus the overall-liking value said given test subject assigned to the weaker test sample and falling within a range of possible overall-liking difference values which may each occur a number of times;

for each possible overall-liking difference value, determining the number of occurrences of the possible overall-liking difference value;

for each possible overall-liking difference value, multiplying the number of occurrences of the possible overall-liking difference value by a probability coefficient to determine a corresponding subset number for each possible overall-liking difference value, the subset number representing the number of test subjects in a correlative, proportionate subset of the test subjects yielding the possible overall-liking difference value that would choose the stronger test sample over the weaker test sample in a forced choice comparison of the two test samples; and totaling the subset numbers corresponding to each of the possible overall-liking difference values to determine the total number of test subjects who would choose the stronger test sample over the weaker test sample in a forced choice comparison of the two test samples.

2. The method of claim 1, further comprising determining a percentage preference value by dividing the total number of test subjects who would choose the stronger test sample over the weaker test sample in a forced choice comparison of the two test samples by the number of test subjects in the test group.

3. The method of claim 1, wherein said stronger test sample has an average overall-liking value and said weaker test sample has an average overall-liking value and wherein the stronger test sample is defined to be the test sample of the two having the larger average overall-liking value.

4. The method of claim 1, wherein said hedonic test data is obtained in integral, Likert scale format and wherein the overall-liking difference value for said given test subject equals the overall-liking value said given test subject assigned to the stronger test sample minus the overall-liking value said test subject assigned to the weaker test sample.

5. The method of claim 1, wherein more than two test samples are sampled by each of said test subjects and wherein predicted forced choice preference results are determined for more than one pair of test samples.

* * * * *